(12) United States Patent
Chiu et al.

(10) Patent No.: US 10,842,354 B2
(45) Date of Patent: Nov. 24, 2020

(54) ENDOSCOPE DEVICE

(71) Applicant: Issa Technology Co., Ltd., Taoyuan (TW)

(72) Inventors: Chi-Wei Chiu, Taoyuan (TW); Rong-Jhe Chen, Taoyuan (TW)

(73) Assignee: ISSA TECHNOLOGY CO., LTD., Taoyuan (TW)

( * ) Notice: Subject to any disclaimer, the term of this patent is extended or adjusted under 35 U.S.C. 154(b) by 0 days.

(21) Appl. No.: 16/416,314

(22) Filed: May 20, 2019

(65) Prior Publication Data

US 2020/0297186 A1  Sep. 24, 2020

(30) Foreign Application Priority Data

Mar. 21, 2019 (TW) .............................. 108109725 A

(51) Int. Cl.
| | | |
|---|---|---|
| *A61B 1/00* | (2006.01) | |
| *G02B 23/24* | (2006.01) | |
| *H04N 5/225* | (2006.01) | |
| *A61B 1/05* | (2006.01) | |

(52) U.S. Cl.
CPC ........ *A61B 1/0011* (2013.01); *A61B 1/00096* (2013.01); *A61B 1/05* (2013.01); *G02B 23/2484* (2013.01); *H04N 5/2253* (2013.01); *H04N 2005/2255* (2013.01)

(58) Field of Classification Search
CPC ............. G02B 23/2484; H04N 5/2253; H04N 2005/2255
See application file for complete search history.

(56) References Cited

U.S. PATENT DOCUMENTS

| | | | | |
|---|---|---|---|---|
| 4,477,636 A | * | 10/1984 | Muroi ................... | C08G 63/52 156/332 |
| 6,049,314 A | * | 4/2000 | Munson .................. | H01Q 1/38 343/846 |
| 2013/0008694 | A1* | 1/2013 | Takamatsu ......... | A61B 1/00027 174/250 |
| 2018/0132704 | A1* | 5/2018 | Yamada .................. | H04N 7/18 |
| 2019/0021581 | A1* | 1/2019 | Ishizuka ............... | H05K 3/3405 |
| 2019/0069767 | A1* | 3/2019 | Mikami ............. | A61B 1/00114 |
| 2019/0348770 | A1* | 11/2019 | Sato .................... | H01R 43/0263 |

* cited by examiner

*Primary Examiner* — Francis Geroleo
*Assistant Examiner* — Christopher Kingsbury Glover
(74) *Attorney, Agent, or Firm* — McClure, Qualey & Rodack, LLP

(57) ABSTRACT

An endoscope device comprises an image capturing unit, a supporting unit, a first and a second coaxial conductive units, and a conductive glue. The image capturing unit has a sensing surface and a back surface with at least two conductive pads thereon. The supporting unit has at least two carrying portions corresponding to the at least two conductive pads respectively. The supporting unit is connected with the back surface of the image capturing unit and extends along a direction approximately orthogonal to the back surface. The first and second coaxial conductive units are located at corresponding carrying portions respectively. The conductive glue covers the first coaxial conductive unit and the conductive pad corresponding to the first coaxial conductive unit, and covers the second coaxial conductive unit and the conductive pad corresponding to the second coaxial conductive unit.

11 Claims, 5 Drawing Sheets

ENDOSCOPE DEVICE

CROSS REFERENCE TO RELATED APPLICATIONS

This Non-provisional application claims priority under 35 U.S.C. § 119(a) on Patent Application No. 108109725 filed in Republic of China on Mar. 21, 2019, the entire contents of which are hereby incorporated by reference.

BACKGROUND

1. Technical Field

The present invention generally relates to an endoscope device, and more particularly, to a micro endoscope device which performs signal transmission through coaxial conductive wires.

2. Description of Related Art

To inspect objects which are implicit, hidden, concealed or interiorly located and hence cannot be directly viewed by human eyes, an endoscope device is usually employed. Specifically, the endoscope device is mostly employed in medical applications, where the micro-sized one can be easily embedded or inserted into human or animal body, and interior organs or tissues can thus be clearly inspected. Furthermore, in addition to medical applications, the endoscope device can be utilized to inspect industrial instruments, building architectures or electronic apparatuses as well.

More particularly, lens of the endoscope device is usually secured to a lens holder and electrically connected with a circuit board. Then, the lens and lens holder, together with the circuit board as a whole, are disposed within a tube-case to form the endoscope device. Accordingly, caliber of the tube-case and hence size of the endoscope device are limited by size of the lens, lens holder and circuit board. If a down-sized endoscope device is required (especially for medical applications where human body is to be inspected), the lens, circuit board or other elements (e.g., conductive wires for signal transmission) have to be shrunk.

However, more efforts must be paid when connecting these shrunk-sized elements to one another. For example, when connecting the circuit board to the conductive wires (especially for wires of diameter smaller than 1-mm) by a welding process, more accuracy is required to align welding points. Furthermore, since these welding points are made tiny and hence lack sufficient size to sustain force applied thereon, undesired cracking may occur to these tiny welding points during operation of the endoscope device. The foregoing descriptions identify a technical problem of the traditional endoscope device.

Consequently, it may be therefore desirable to have an improved endoscope device that is able to cure the above-identified problem. Such an improved endoscope device should have its structure remain rigid as its size shrinks.

SUMMARY OF THE INVENTION

Given the above, a purpose of the present invention directs to provide an endoscope device which can retain its rigidity even in a micro-size. With a rigid structure, such an endoscope device can always achieve good electrical characteristics free of structural damage.

To achieve the above-identified purpose, the present invention may provide an endoscope device, which comprises an image capturing unit, a supporting unit, a first coaxial conductive unit and a second coaxial conductive unit. The image capturing unit has a sensing surface and a back surface opposite to each other, the back surface has at least two conductive pads, the supporting unit is connected with the back surface of the image capturing unit and extends along a direction approximately orthogonal to the back surface, and having at least two carrying portions which correspond to the at least two conductive pads respectively, the first coaxial conductive unit is electrically connected with and corresponding to one of the at least two conductive pads, and being located at one of the at least two carrying portions of the supporting unit, and the second coaxial conductive unit is electrically connected with and corresponding to the other one of the at least two conductive pads, and being located at the other one of the at least two carrying portions of the supporting unit.

According to an example of the present invention, the supporting unit further comprises a base plate having a first surface and a second surface, the first surface refers to one of the at least two carrying portions, and the second surface refers to the other one of the at least two carrying portions.

According to an example of the present invention, the supporting unit further comprises a base plate having a first surface and a second surface opposite to each other, and a spacer plate being disposed on the first surface of the base plate, and separating one of the at least two carrying portions from the other one thereof.

According to an example of the present invention, the first surface of the base plate further comprises a containing region, the containing region has a surface with a different elevation from the first surface of the base plate.

According to an example of the present invention, the endoscope device further comprises an electronic element disposed at the containing region of the supporting unit, located between the image capturing unit and the first coaxial conductive unit, and/or located between the image capturing unit and the second coaxial conductive unit.

According to an example of the present invention, the endoscope device further comprises a conductive glue covering and electrically connecting the first coaxial conductive unit with the corresponding conductive pad and the corresponding electrode of the electronic element, and/or covering and electrically connecting the second coaxial conductive unit with the corresponding conductive pad and the corresponding electrode of the electronic element.

According to an example of the present invention, the interface between the first coaxial conductive unit and the corresponding conductive pad, and/or the interface between the first coaxial conductive unit and the corresponding electrode of the electronic element, and/or the interface between the second coaxial conductive unit and the corresponding conductive pad, and/or the interface between the second coaxial conductive unit and the corresponding electrode of the electronic element, are electrically connected by laser welding.

According to an example of the present invention, electronic element is a surface-adhesive capacitor or surface-mounted capacitor.

According to an example of the present invention, the endoscope device further comprises an adhesive glue, covering and securing the first coaxial conductive unit to the supporting unit, and/or covering and securing the second coaxial conductive unit to the supporting unit.

According to an example of the present invention, the adhesive glue is light-curing glue, heat-melt glue or mixture-curing glue.

According to an example of the present invention, the supporting unit further comprises a protective cover enclosing and covering at least a part of the carrying portions.

According to an example of the present invention, the endoscope device further comprises a conductive glue covering and electrically connecting the first coaxial conductive unit with the corresponding conductive pad, and/or covering and electrically connecting the second coaxial conductive unit with the corresponding conductive pad.

According to an example of the present invention, the interface between the first coaxial conductive unit and the corresponding conductive pad, and/or the interface between the second coaxial conductive unit and the corresponding conductive pad, are electrically connected by laser welding.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The parts in the drawings are not necessarily drawn to scale, the emphasis instead being placed upon clearly illustrating the principles of at least one embodiment. In the drawings, like reference numerals designate corresponding parts throughout the various diagrams, and all the diagrams are schematic.

DETAILED DESCRIPTION

Reference will now be made to the drawings to describe various inventive embodiments of the present disclosure in detail, wherein like numerals refer to like elements throughout.

Figure 1A:
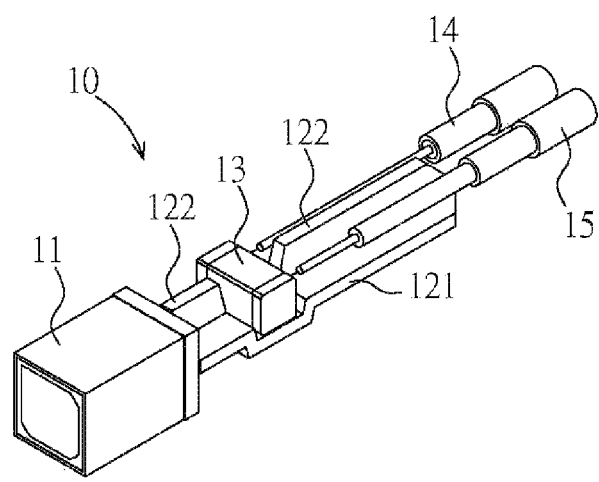
FIG. 1A is a schematic perspective view of an endoscope device according to the first embodiment of the present invention.
Figure 1B:
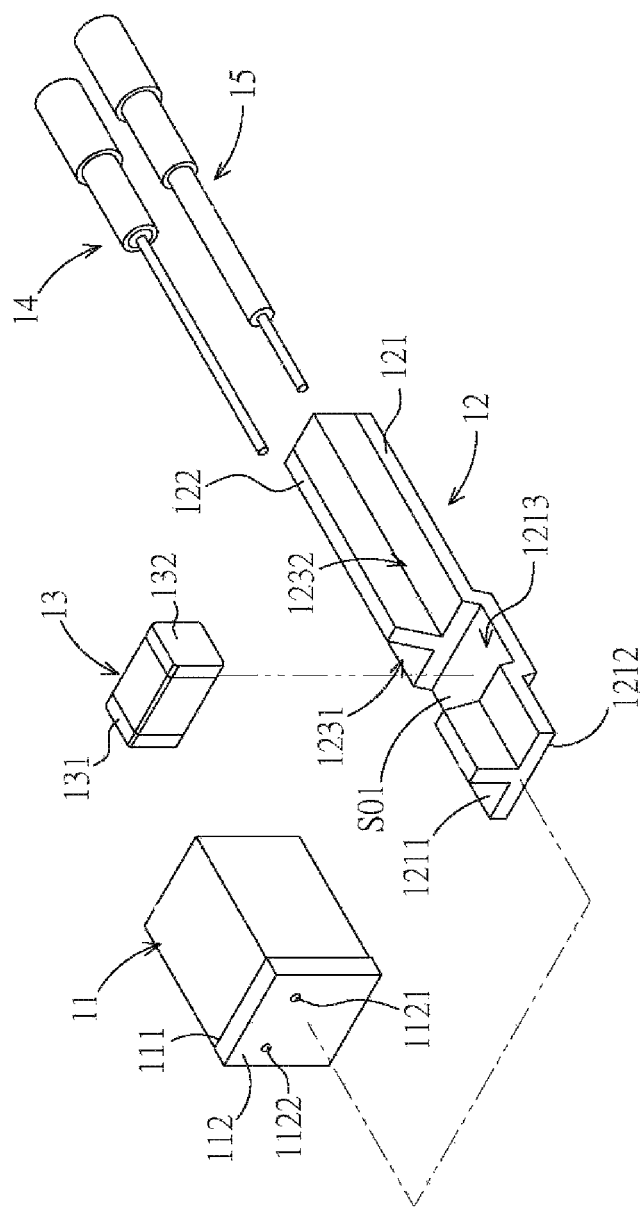
FIG. 1B is an exploded view of the endoscope device illustrated in FIG. 1A.

FIG. 1A is a schematic perspective view of an endoscope device 10 according to the first embodiment of the present invention, and FIG. 1B is an exploded view of the endoscope device 10 illustrated in FIG. 1A. Referring to both FIGS. 1A and 1B, the endoscope device 10 of the first embodiment may include an image capturing unit 11, a supporting unit 12 (also termed as "sustaining unit", "retaining unit" or "holding unit"), an electronic element 13, a first coaxial conductive unit 14, a second coaxial conductive unit 15 and conductive glue.

The image capturing unit 11 may have a sensing surface 111 and a back surface 112. Lens and sensing elements such as CMOS (complementary metal-oxide-semiconductor) or CCD (charge coupled device) may be disposed on the sensing surface 111 so as to perform image sensing and capturing. Furthermore, the back surface 112 may have a plurality of conductive pads (also termed as "connecting pads", "bonding pads", "solder pads" or "electrode pads") so as to perform signal transmission or power transmission between the sensing element and external elements. In the first embodiment, the back surface 112 may have a first conductive pad 1121 and a second conductive pad 1122.

The supporting unit 12 may be connected with the back surface 112 of the image capturing unit 11. Wherein, the supporting unit 12 may extend along a direction approximately orthogonal to the back surface 112 of the image capturing unit 11. Specifically, in the first embodiment, the supporting unit 12 may be connected with the back surface 112 of the image capturing unit 11 by gluing (i.e., adhesive bonding), locking (i.e., lock-fitting) or joggle-jointing (i.e., mortise jointing) with the aids of mortise/tenon, latches, or clamping elements. More particularly, the supporting unit 12 may have a base plate 121 and a spacer plate 122. The base plate 121 may have a first surface 1211 and a second surface 1212. Furthermore, the spacer plate 122 may be vertically disposed on the first surface 1211 of the base plate 121. In view of the above arrangements of the base plate 121 and the spacer plate 122, two spaces may be defined at both sides of the spacer plate 122. The defined spaces may refer to a first carrying portion 1231 and a second carrying portion 1232, respectively.

As connecting the back surface 112 of the image capturing unit 11 with the supporting unit 12, the first conductive pad 1121 on the back surface 112 may have a location corresponding to the first carrying portion 1231 of the supporting unit 12, whereas the second conductive pad 1122 on the back surface 112 may have a location corresponding to the second carrying portion 1232 of the supporting unit 12. The first carrying portion 1231 and the second carrying portion 1232 are separated from each other (separated by the spacer plate 122), which means, the first conductive pad 1121 and the second conductive pad 1122 are also separated from each other. Accordingly, electrical insulation may be provided between the first and second conductive pads 1121 and 1122, and short-circuit may thus be prevented.

In addition, the base plate 121 may further include a containing region 1213. The containing region 1213 may have a planar surface S01 to allow and facilitate other elements to be disposed, placed or installed thereon. In the present embodiment, the surface S01 of the containing region 1213 may have a different elevation from the first surface 1211 of the base plate 121. For example, the surface S01 of the containing region 1213 may be slightly lower than the first surface 1211 of the base plate 121. In this manner, an electronic element 13 may be easily disposed, placed or installed on the surface S01 of the containing region 1213. Specifically, the electronic element 13 may be a capacitor for filtering incoming signal. For example, the electronic element 13 may be a surface-mounted capacitor (also termed as "chip capacitor"). Furthermore, the electronic element 13 may have a first electrode 131 and a second electrode 132 which may correspond to the first carrying portion 1231 and the second carrying portion 1232 respectively.

More particularly, the first coaxial conductive unit 14 may correspond to the first conductive pad 1121, and may be located on the first carrying portion 1231 of the supporting unit 12. Likewise, the second coaxial conductive unit 15 may correspond to the second conductive pad 1122, and may be located on the second carrying portion 1232 of the supporting unit 12. The first coaxial conductive unit 14 may be substantially same as the second coaxial conductive unit 15 in structure. In one example, each of the first and second coaxial conductive units 14 and 15 may have a structure composed of a central conductive wire, an insulating layer, a shielding layer and a protective cover (in the order of inside-out). More particularly, the central conductive wire may have copper core, while the shielding layer may have metal weaving fabrics or aluminum foils. In the present embodiment, the central conductive wire may have a diameter of approximately 0.05 millimeter, which is suitable for a micro-sized endoscope device 10. Given the above, all the first conductive pad 1121, the first electrode 131 and the first coaxial conductive unit 14 may be located at or correspond to the first carrying portion 1231. On the other hand, all the second conductive pad 1122, the second electrode 132 and the second coaxial conductive unit 15 may be located at or correspond to the second carrying portion 1232. Based on the above arrangement, connecting points of concerned elements (i.e., the elements to be electrically connected) may be separated from one another, which may therefore avoid undesired short-circuit between these connecting points. Meanwhile, efficiency for manufacturing process may be also enhanced.

Rather than welding process, the first conductive pad 1121, the first electrode 131 of the electronic element 13 and the first coaxial conductive unit 14 may be electrically connected with one another through the conductive glue (in the same manner, the second conductive pad 1122, the second electrode 132 and the second coaxial conductive unit 15 may be also electrically connected with one another through the conductive glue). To discuss in more detail, the electronic element 13 may be disposed between the image capturing unit 11 and the first and second coaxial conductive units 14 and 15 and need to be connected with one another. However, due to micro-size of the first and second coaxial conductive unit 14 and 15, it may be difficult to apply soldering or welding process to achieve the above connections. Accordingly, conductive glue may be applied instead of welding process, which may accurately and more rigidly connect the first and second coaxial conductive units 14 and 15 with corresponding elements or portions (i.e., connect with the first and second conductive pads 1121 and 1122, and/or connect with the first and second electrodes 131 and 132).

Furthermore, the first coaxial conductive unit 14 and the second coaxial conductive unit 15 may be respectively fixed or secured to the supporting unit 12 through adhesive glue, for example, light-curing glue (e.g., UV glue), heat-melt glue, thermosetting glue or mixture-curing glue (e.g., AB glue with epoxy resin). In this manner, the endoscope device 10 may reach a more solid or rigid structure. In other words, elements or portions of interest (which need conduct electrical signals) may be electrically connected with one another through conductive glue, and conductive glue may also serve to fix or secure these elements or portions. On the other hand, other elements or portions (which need not conduct electrical signals) may be fixed or secured through adhesive glue, but not conductive glue. In this manner, manufacturing process may be simplified, whereas the endoscope device 10 may still remain structural firmness or rigidity.

Skilled persons in this art would realize that, the concerned elements or portions may be electrically connected with one another by other ways, for example, by laser welding process. That is, electrical connections for respective interfaces between concerned elements (i.e., the interface between the first conductive pad 1121 and the first electrode 131, the interface between the first coaxial conductive unit 14 and the first electrode 131, the interface between the second conductive pad 1122 and the second electrode 132, and the interface between the second coaxial conductive unit 15 and the second electrode 132), may be achieved by laser welding process. In one example, the concerned elements or portions may be firstly disposed to contact each other, and afterwards, laser welding process may be performed to connect these elements or portions. In another example, exterior conductive elements (e.g., metal conductive wires) may be firstly disposed between the concerned elements or portions, then, laser welding process may be performed to form welding points (also termed as "connecting points"), through which these concerned elements and the exterior conductive elements are connected.

Per the foregoing descriptions, the supporting unit 12 may serve to support (or sustain, hold, bear, carry) the first and second coaxial conductive units 14 and 15. In addition, various amounts of exterior connecting points (or welding points) may be added to suit or fit various types of image capturing units, and the supporting unit 12 may thus be modified or change its arrangement correspondingly.

Figure 2A:
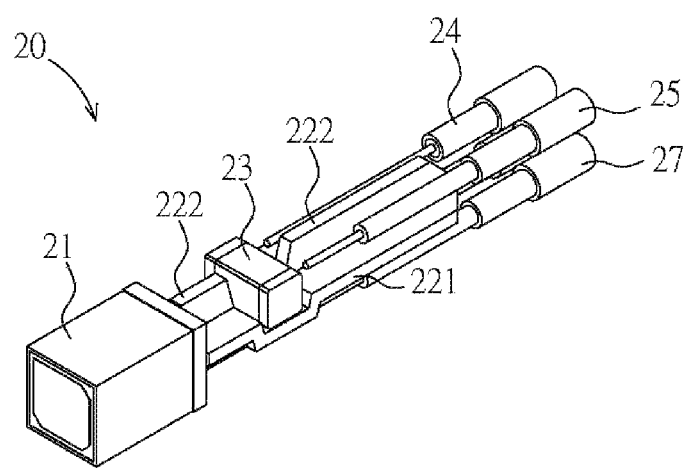
FIG. 2A is a schematic perspective view of an endoscope device according to the second embodiment of the present invention.
Figure 2B:
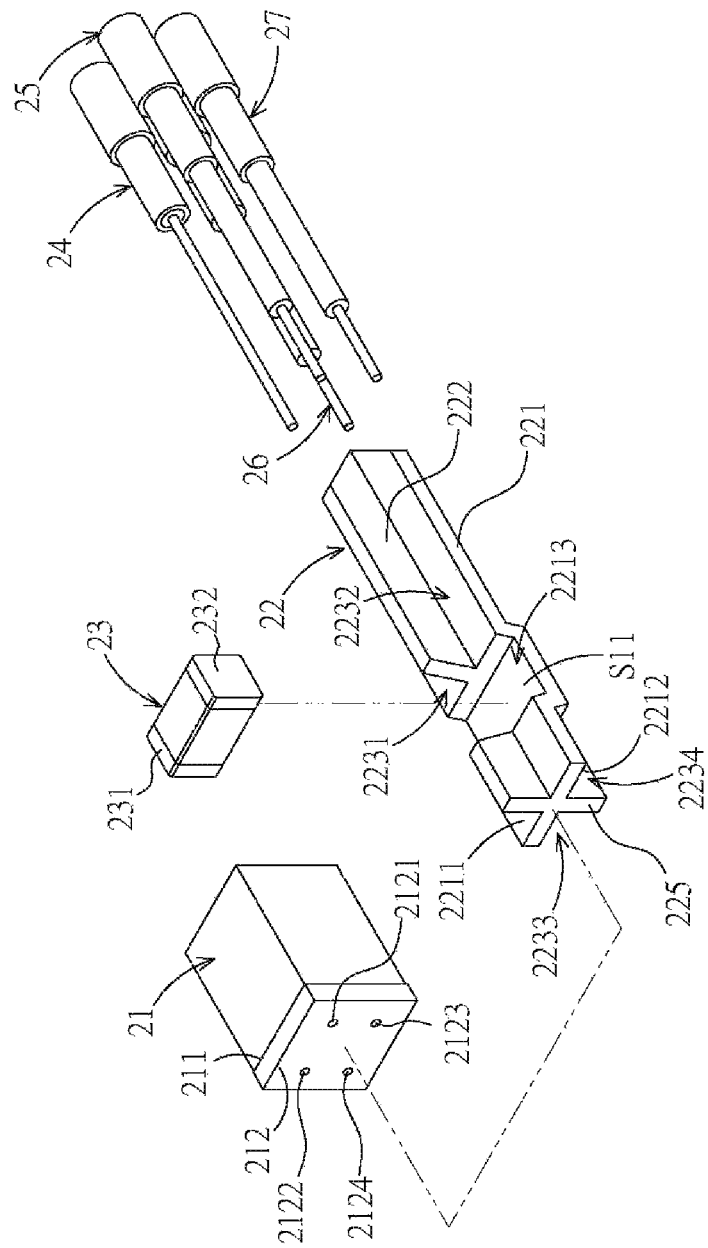
FIG. 2B is an exploded view of the endoscope device illustrated in FIG. 2A.

FIG. 2A is a schematic perspective view of an endoscope device 20 according to the second embodiment of the present invention, and FIG. 2B is an exploded view of the endoscope device 20 illustrated in FIG. 2A. Referring to both FIGS. 2A and 2B, the endoscope device 20 of the second embodiment may include an image capturing unit 21, a supporting unit 22, an electronic element 23, a first coaxial conductive unit 24, a second coaxial conductive unit 25, a third coaxial conductive unit 26, a fourth coaxial conductive unit 27, conductive glue and adhesive glue. Elements or portions of the endoscope device 20 of the second embodiment, in both function and structure, may be similar to or same as corresponding ones of the endoscope device 10 of the first embodiment. Therefore, these elements or portions are not further discussed.

The image capturing unit 21 may have a sensing surface 211 and a back surface 212, which may be similar to the image capturing unit 11 of the first embodiment except that, the back surface 212 of the image capturing unit 21 may have at least two more conductive pads (i.e., the back surface 212 may have at least four conductive pads). The at least four conductive pads of the back surface 212 may refer to the first, the second, the third and the fourth conductive pads 2121, 2122, 2123 and 2124.

Furthermore, the supporting unit 22 may be connected with the back surface 212 of the image capturing unit 21. Moreover, the supporting unit 22 may have a base plate 221, a first spacer plate 222 and a second spacer plate 225. Which means, comparing to the supporting unit 11 of the first embodiment, the supporting unit 22 of the second embodiment may have one more spacer plate (i.e., the second spacer plate 225).

As connecting the back surface 212 of the image capturing unit 21 with the supporting unit 22, the first, second, third and fourth conductive pads 2121, 2122, 2123 and 2124 on the back surface 212 may have locations corresponding to the first, second, third and fourth carrying portions 2231, 2232, 2233 and 2234 of the supporting unit 22 respectively. The first, second, third and fourth carrying portions 2231, 2232, 2233 and 2234 are separated from one another (separated by the base plate 221, the first and second spacer plates 222 and 225), which means, the first, second, third and fourth conductive pads 2121, 2122, 2123 and 2124 are also separated. Accordingly, electrical insulation may be provided between the first, second, third and fourth conductive pads 2121, 2122, 2123 and 2124, and short-circuit may thus be avoided.

The base plate 221 may further include a containing region 2213. Furthermore, the surface S11 of the containing region 2213 may have a different elevation from the first surface 2211 of the base plate 221 (the elevations of the surface S11 and first surface 2211 are measured with respect to a side view of the endoscope device 20). For example, the surface S11 of the containing region 2213 may be slightly lower than the first surface 2211 of the base plate 221. In this manner, an electronic element 23 may be easily disposed, placed or installed on the surface S11 of the containing region 2213. Specifically, the electronic element 23 may have a first electrode 231 and a second electrode 232 which may correspond to the first carrying portion 2231 and the second carrying portion 2232 respectively. In addition, the electronic element 23 may be a capacitor for filtering incoming signal, which may be similar to or same as the electronic element 13 of the first embodiment.

More particularly, the first coaxial conductive unit 24 may correspond to the first conductive pad 2121, and may be located on the first carrying portion 2231 of the supporting unit 22. Likewise, the second, third and fourth coaxial conductive units 25, 26 and 27 may correspond to the second, third and fourth conductive pads 2122, 2123 and 2124. Furthermore, the second, third and fourth coaxial conductive units 25, 26 and 27 may be located on the second, third and fourth carrying portions 2232, 2233 and 2234 of the supporting unit 22. The first, second, third and fourth coaxial conductive units 24, 25, 26 and 27 may be substantially the same in structure. In one example, each of the first, second, third and fourth coaxial conductive units 24, 25, 26 and 27 may have a structure comprising a central conductive wire, an insulating layer, a shielding layer and a protective cover (which may be disposed in the order of inside-out). Furthermore, to meet various requirements, each of the central conductive wire, the insulating layer and the shielding layer may be selectively exposed.

Given the above, all the first conductive pad 2121, the first electrode 231 and the first coaxial conductive unit 24 may be located at or correspond to the first carrying portion 2231. On the other hand, all the second conductive pad 2122, the second electrode 232 and the second coaxial conductive unit 25 may be located at or correspond to the second carrying portion 2232. Likewise, the third conductive pad 2123 and the third coaxial conductive unit 26 may be located at or correspond to the third carrying portion 2233. In the same fashion, the fourth conductive pad 2124 and the fourth coaxial conductive unit 27 may be located at or correspond to the fourth carrying portion 2234. By way of the above arrangement, connecting points (or welding points) between concerned elements (the elements to be electrically connected) may be well separated from one another. Therefore, undesired short-circuit between these connecting points (or welding points) may be well prevented, and manufacturing process may be well enhanced.

In addition, like the first embodiment, the endoscope device 20 of the second embodiment may apply conductive glue to electrically connect and secure all concerned elements or portions (i.e., the conductive pads 2121, 2122, 2123 and 2124 of the image capturing unit 21, the electrodes 231 and 232 of the electronic element 23, and the coaxial conductive units 24, 25, 26 and 27). Furthermore, the shielding layer of each of the coaxial conductive units 24, 25, 26 and 27 may be electrically connected with the ground through the conductive glue.

Figure 2C:
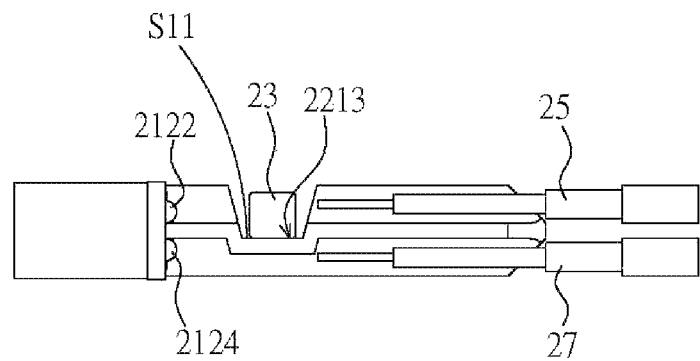
FIG. 2C is a side view of the endoscope device illustrated in FIG. 2A.

FIG. 2C is a side view of the endoscope device 20 illustrated in FIG. 2A. Referring to FIG. 2C, the electronic element 23 may be disposed between the image capturing unit 21 and the coaxial conductive units 25 and 27 (also coaxial conductive units 24 and 26). However, due to micro-size of the coaxial conductive units 24, 25, 26 and 27, it may be difficult to apply soldering or welding process thereto. Instead, conductive glue may be applied to electrically connect the coaxial conductive units 24, 25, 26 and 27 to corresponding elements or portions (i.e., the conductive pads 2121, 2122, 2123 and 2124 and the electrodes 231 and 232). In other words, the coaxial conductive units 24, 25, 26 and 27, the electronic element 23 and the conductive pads 2121, 2122, 2123 and 2124 may not contact one another in substance, but electrically connected with one another through conductive glue.

In another example, the coaxial conductive units 24, 25, 26 and 27, the electrodes 231 and 232 of the electronic element 23, and the conductive pads 2121, 2122, 2123 and 2124 of the imaging capturing unit 21 may be electrically connected with one another by laser-welding process. On the other hand, the coaxial conductive units 24, 25, 26 and 27 may be respectively fixed or secured to the supporting unit 22 through an adhesive glue, for example, a light-curing glue (e.g., UV glue), a hot-melt glue, a thermosetting glue or a mixture-curing glue (e.g., AB glue). In this manner, the endoscope device 20 of the second embodiment may achieve a more solid or rigid structure, like the endoscope device 10 of the first embodiment.

Figure 3:
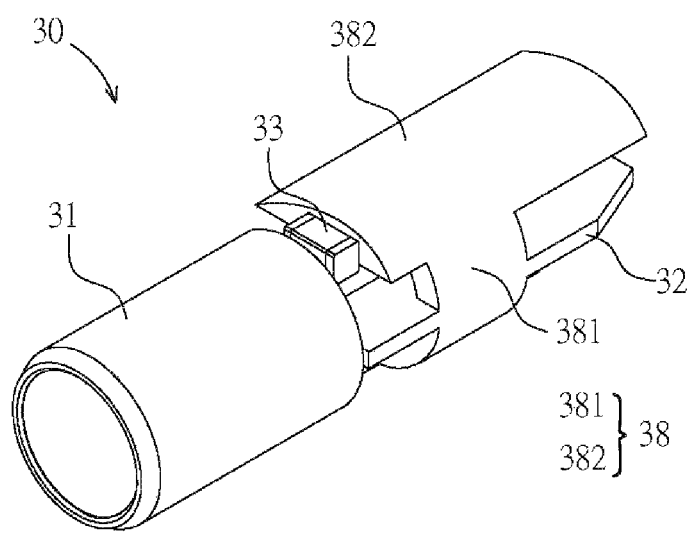
FIG. 3 is a schematic perspective view of an endoscope device according to the third embodiment of the present invention.

FIG. 3 is a schematic perspective view of an endoscope device 30 according to the third embodiment of the present invention. Referring to FIG. 3, the endoscope device 30 may be similar to the endoscope devices 10 and 20 of the first and second embodiments, which may include an image capturing unit 31, a supporting unit 32, an electronic element 33 and coaxial conductive units (not shown). However, unlike the image capturing units 11 and 21 with the form of cuboid, the image capturing unit 31 of the third embodiment may take the form of a cylinder.

In addition, the endoscope device 30 of the third embodiment may further include a protective cover 38, which may be connected with the supporting unit 32 and enclose (or surround) the carrying portions of the supporting unit 32. The protective cover 38 may have a connecting portion 381 and a cap 382. The connecting portion 381 may serve to connect with the base plate of the supporting unit 32, while the cap 382 may be arranged between the connecting portion 381 and the spacer plate. Since the protective cover 38 is disposed in a manner enclosing or surrounding the carrying portions, the resulting carrying portions may take the form of a channel, and coaxial conductive units may be easily disposed therein.

Even though numerous characteristics and advantages of certain inventive embodiments have been set out in the foregoing description, together with details of the structures and functions of the embodiments, the disclosure is illustrative only. Changes may be made in detail, especially in matters of arrangement of parts, within the principles of the present disclosure to the full extent indicated by the broad general meaning of the terms in which the appended claims are expressed.

What is claimed is:
1. An endoscope device, comprising:
an image capturing unit, having a sensing surface and a back surface opposite to each other, the back surface has at least two conductive pads;

a supporting unit, being connected with the back surface of the image capturing unit and extending along a direction approximately orthogonal to the back surface, and having at least two carrying portions which correspond to the at least two conductive pads respectively, a base plate which has a first surface and a second surface, the first surface refers to one of the at least two carrying portions, and the second surface refers to the other one of the at least two carrying portions, and a containing region which has a surface with a different elevation from the first surface located on the first surface;

a first coaxial conductive unit, corresponding to and being electrically connected with one of the at least two conductive pads, and located at one of the at least two carrying portions of the supporting unit; and a second coaxial conductive unit, corresponding to and being electrically connected with the other one of the at least two conductive pads, and located at the other one of the at least two carrying portions of the supporting unit;

an electronic element, being disposed at the containing region of the supporting unit, located between the image capturing unit and the first coaxial conductive unit, and/or located between the image capturing unit and the second coaxial conductive unit, wherein, the height of the electronic element is greater than or equal to half of the longest side width of the image capturing unit.

2. The endoscope device of claim 1, further comprising:
a conductive glue, covering and electrically connecting the first coaxial conductive unit with the corresponding conductive pad and a corresponding electrode of the electronic element, and/or covering and electrically connecting the second coaxial conductive unit with the corresponding conductive pad and a corresponding electrode of the electronic element.

3. The endoscope device of claim 1, wherein the interface between the first coaxial conductive unit and the corresponding conductive pad, and/or the interface between the first coaxial conductive unit and the corresponding electrode of the electronic element, and/or the interface between the second coaxial conductive unit and the corresponding conductive pad, and/or the interface between the second coaxial conductive unit and the corresponding electrode of the electronic element, are electrically connected by laser welding.

4. The endoscope device of claim 1, wherein the electronic element is a surface-adhesive capacitor or a surface-mounted capacitor.

5. The endoscope device of claim 1, further comprising:
an adhesive glue, covering the first coaxial conductive unit and securing the first coaxial conductive unit to the supporting unit, and/or covering the second coaxial conductive unit and securing the second coaxial conductive unit to the supporting unit.

6. The endoscope device of claim 5, wherein the adhesive glue is a light-curing glue, a heat-melt glue or a mixture-curing glue.

7. The endoscope device of claim 1, wherein the supporting unit further comprising:
a protective cover, enclosing and covering at least a part of the carrying portions.

8. The endoscope device of claim 1, further comprising:
a conductive glue, covering and electrically connecting the first coaxial conductive unit with the corresponding conductive pad, and/or covering and electrically connecting the second coaxial conductive unit with the corresponding conductive pad.

9. The endoscope device of claim 1, wherein the interface between the first coaxial conductive unit and the corresponding conductive pad, and/or the interface between the second coaxial conductive unit and the corresponding conductive pad, are electrically connected by laser welding.

10. The endoscope device of claim 1, wherein the supporting unit further comprising:
a base plate, having a first surface and a second surface opposite to each other; and
a spacer plate, being disposed on the first surface of the base plate, and separating one of the at least two carrying portions from the other one.

11. The endoscope device of claim 1, wherein the image capturing unit has a lens and a sensing element, which are disposed on the sensing surface so as to perform image sensing and capturing.

* * * * *